(12) United States Patent
Shepard

(10) Patent No.: US 8,449,176 B2
(45) Date of Patent: *May 28, 2013

(54) AUTOMATED BINARY PROCESSING OF THERMOGRAPHIC SEQUENCE DATA

(75) Inventor: Steven Shepard, Southfield, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 517 days.

This patent is subject to a terminal disclaimer.

(21) Appl. No.: 12/763,992

(22) Filed: Apr. 20, 2010

(65) Prior Publication Data

US 2010/0235115 A1  Sep. 16, 2010

Related U.S. Application Data

(63) Continuation-in-part of application No. 11/497,988, filed on Aug. 1, 2006, now Pat. No. 7,699,521.

(60) Provisional application No. 60/704,258, filed on Aug. 1, 2005.

(51) Int. Cl.
  *G01N 25/72* (2006.01)
  *G01K 1/00* (2006.01)
  *G01K 17/00* (2006.01)
  *G01K 3/00* (2006.01)

(52) U.S. Cl.
  USPC ............... 374/124; 374/120; 374/5; 374/137; 702/130; 702/136

(58) Field of Classification Search
  USPC ............... 374/120, 124, 137, 5; 702/130, 136
  See application file for complete search history.

(56) References Cited

U.S. PATENT DOCUMENTS

| | | | |
|---|---|---|---|
| 5,282,195 A | | 1/1994 | Hood et al. |
| 6,100,101 A * | | 8/2000 | Marathe et al. ............... 438/14 |
| 6,516,084 B2 | | 2/2003 | Shepard |
| 6,712,502 B2 | | 3/2004 | Zalameda et al. |
| 6,751,342 B2 | | 6/2004 | Shepard |
| 8,047,709 B1 * | | 11/2011 | Vaccaro ........................ 374/45 |
| 2002/0044679 A1 | | 4/2002 | Shepard |
| 2002/0128789 A1 | | 9/2002 | Houge et al. |
| 2002/0172410 A1 | | 11/2002 | Shepard |
| 2004/0220740 A1 * | | 11/2004 | Srivastava et al. ............. 702/6 |
| 2008/0068590 A1 * | | 3/2008 | Martinez et al. .............. 356/51 |
| 2009/0164811 A1 * | | 6/2009 | Sharma et al. ............... 713/310 |
| 2010/0131225 A1 * | | 5/2010 | Carlson ....................... 702/130 |

OTHER PUBLICATIONS

Office Action dated Sep. 12, 2008 for U.S. Appl. No. 11/497,988.
Office Action dated Aug. 17, 2009 for U.S. Appl. No. 11/497,988.
Office Action dated Mar. 6, 2009 for U.S. Appl. No. 11/497,988.
Advisory Action dated Nov. 2, 2009 for U.S. Appl. No. 11/497,988.

* cited by examiner

*Primary Examiner* — Mirellys Jagan
(74) *Attorney, Agent, or Firm* — Honigman Miller Schwartz and Cohn LLP

(57) ABSTRACT

A method for processing thermographic data is disclosed including thermally disturbing a specimen of unknown quality, collecting thermal data from said specimen, converting the collected data into a measure of variance and comparing the variance from the sample of unknown quality against the variance of a sample of known quality in order to determine if the quality of the specimen of unknown quality is acceptable.

19 Claims, 14 Drawing Sheets

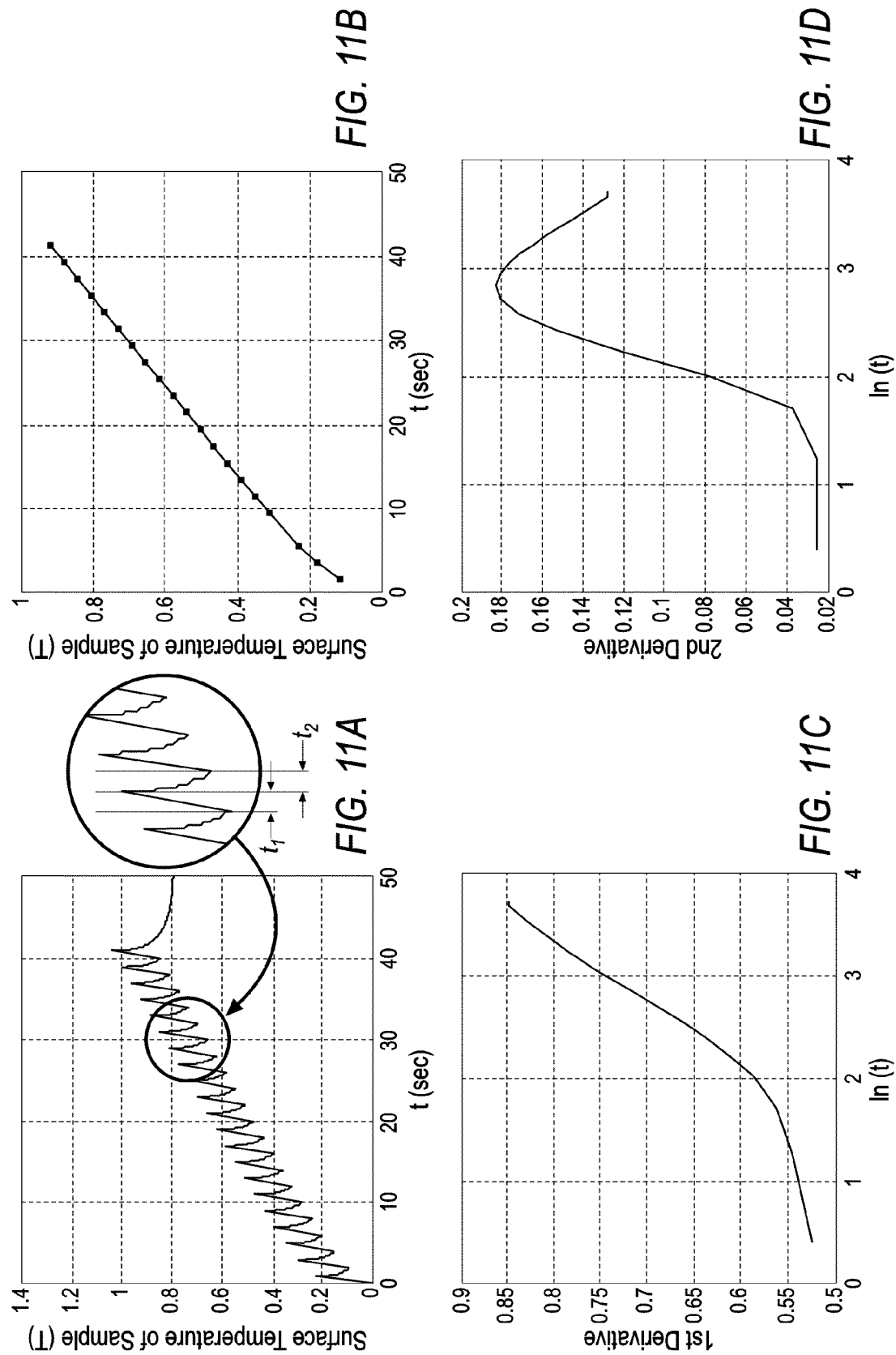

Loose Fit (More Data Scatter)

Tight Fit (Less Data Scatter)

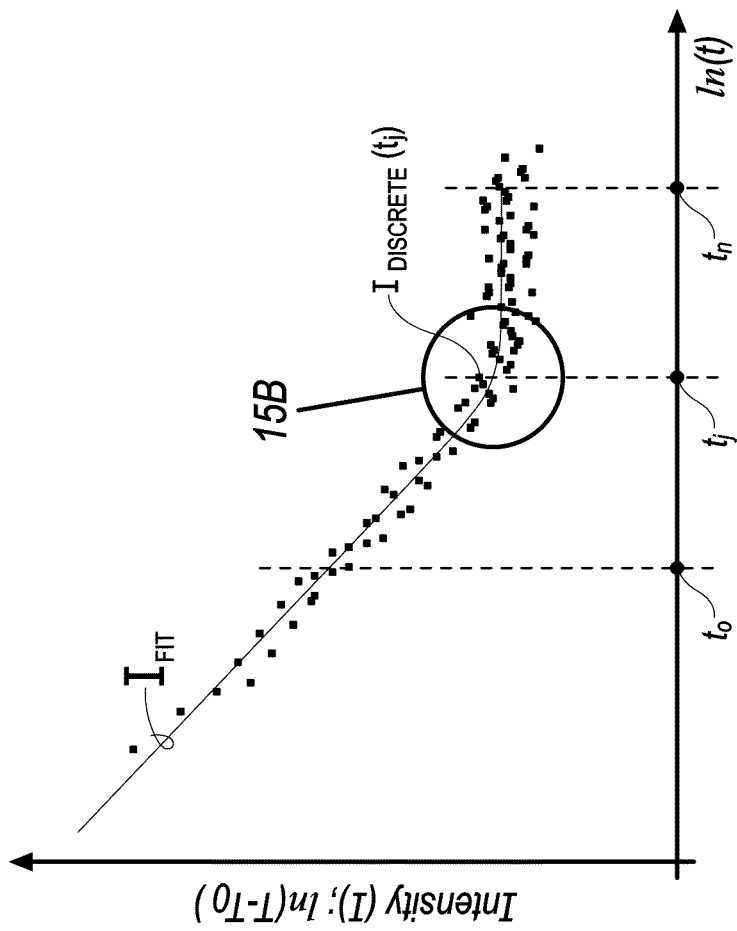
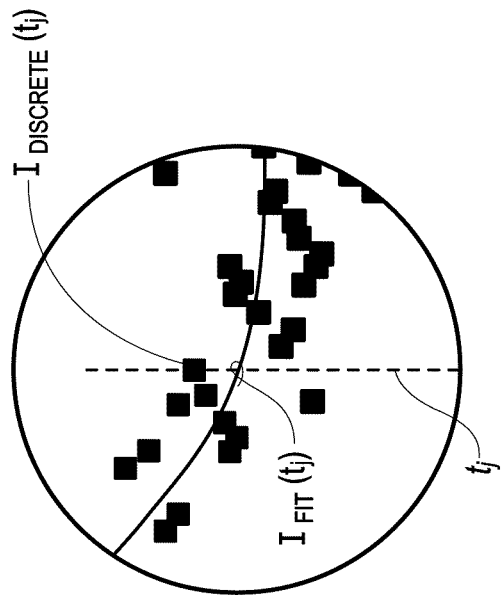
FIG. 15A
FIG. 15B

AUTOMATED BINARY PROCESSING OF THERMOGRAPHIC SEQUENCE DATA

RELATED APPLICATION

This application is a continuation-in-part of U.S. patent application Ser. No. 11/497,988 filed Aug. 1, 2006, now U.S. Pat. No. 7,699,521 issued Apr. 20, 2010, which claims priority to U.S. provisional patent application No. 60/704,258, filed on Aug. 1, 2005.

FIELD OF THE DISCLOSURE

This invention generally relates to imaging and more particularly relates to thermal imaging of a sample using infrared radiation.

BACKGROUND

Thermographic nondestructive testing methods are known and are used to create images of a sample's subsurface features in order to detect internal flaws or features, measure a sample's thickness, thermal diffusivity, or other characteristics of subsurface features (such as depth and/or lateral size of subsurface features). However, existing techniques do not allow robust automated segmentation of subsurface defects from a data sequence without a prior knowledge of the thermophysical properties of the sample, visual interpretation by an operator, or comparison to a known defect-free sample.

BRIEF DESCRIPTION OF THE DRAWINGS

Embodiments of the disclosure will now be described, by way of example, with reference to the accompanying exemplary drawings, wherein:

FIG. 11A is a graph depicting the surface temperature of a sample when modulated by a modulating heat source;

FIG. 11B is a monotonically ascending function that is created by sampling a point during each saw tooth's inactive cycle that has the same time delay (within each saw tooth) after the heating source is inactivated;

FIGS. 11C and 11D are $1^{st}$ and $2^{nd}$ derivatives, respectively, of the function shown in FIG. 11B.

FIG. 15A is a graphical representation of a data scatter plot.

FIG. 15B is an enlargement of the encircled portion of FIG. 15A.

DETAILED DESCRIPTION

Figure 1:
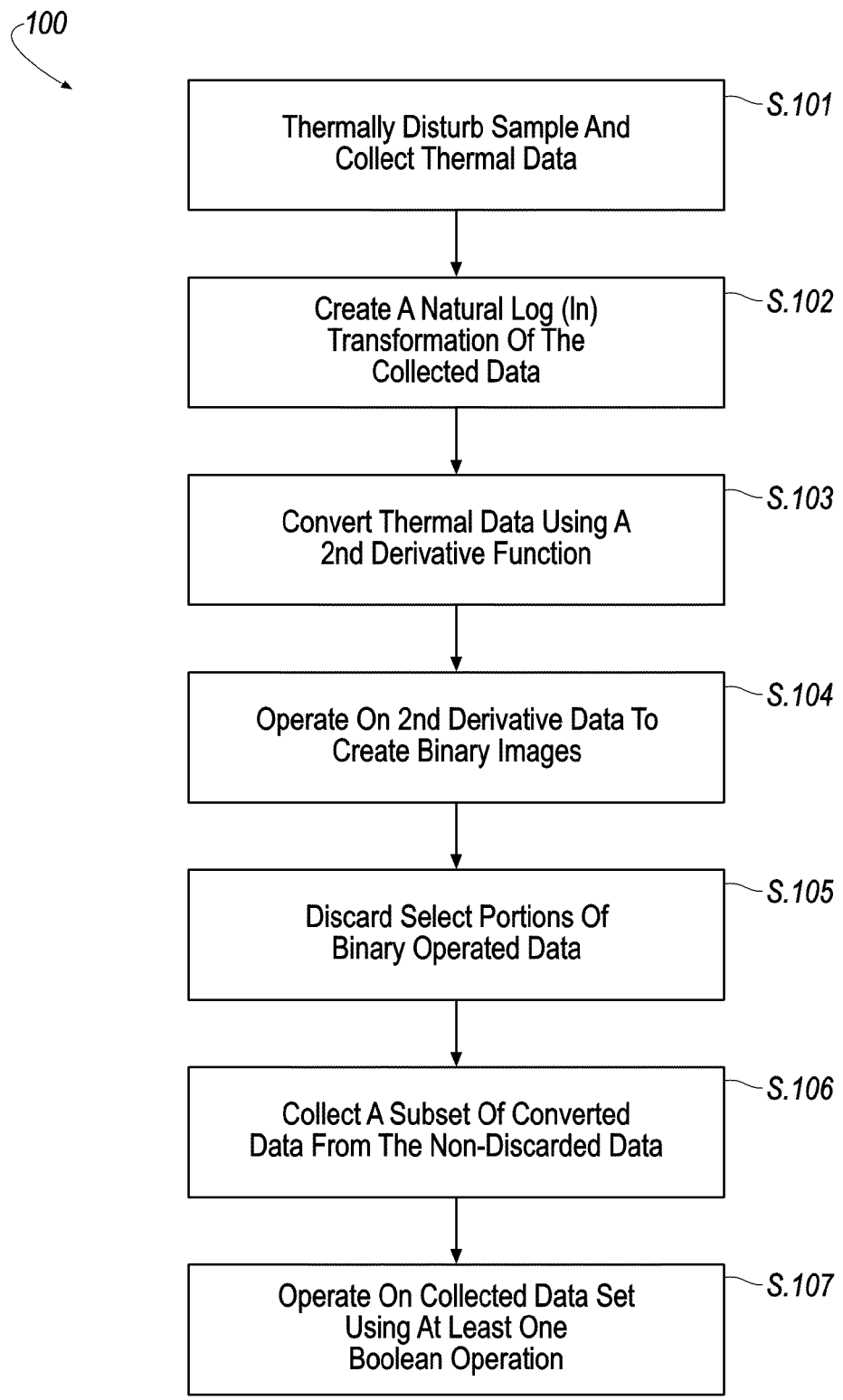
FIG. 1 is a logic flow diagram of automated binary processing of thermographic sequence data according to an embodiment.
Figure 5:
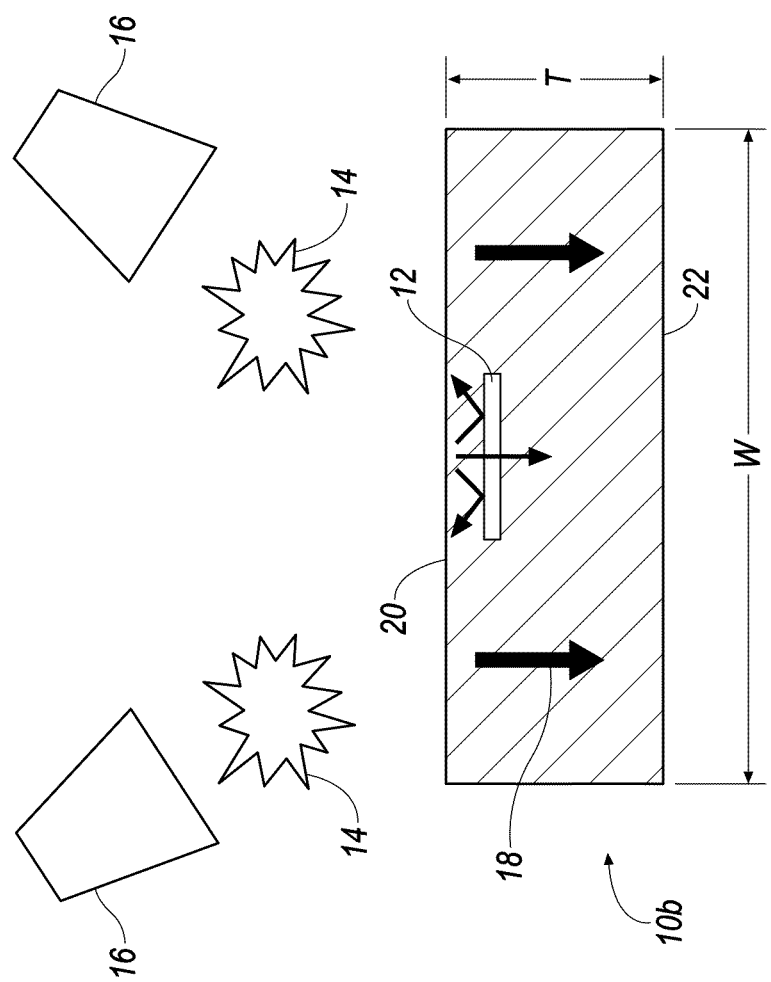
FIG. 5 is a representative diagram of a thermographic imaging system heating a test sample that includes an internal defect.

Referring to FIG. 1, the present invention is directed to a novel thermographic nondestructive testing procedure 100 that provides a means for quantifying a state or characteristic of a sample 10a, 10b (FIGS. 3 and 5, respectively), such as, for example, the presence of a subsurface defect 12 by referencing one or more shape characteristics of a logarithmic $2^{nd}$ derivative thermographic signal 106 (FIG. 2) radiated from the sample. One such sample 10a, 10b characteristic includes the presence or absence of sub-surface defect(s) 12 (FIG. 5). However, it will be readily obvious to one skilled in the art that other characteristics can also be readily detected and quantified by the present invention. The behavior of the $2^{nd}$ derivative signal 106 carries information that can be used to predict subsurface sample characteristics without a priori knowledge of the attributes of the sample 10a, 10b.

A logarithmic $2^{nd}$ derivative is a far more robust and sensitive indicator of the subsurface state of a sample than either direct viewing of the infrared image sequence after heating the sample, or analysis of the pixel temperature-time history (or the natural logarithm of the temperature-time history). Furthermore, it provides valuable information about the sample even in the case where no defect is present, so that a single pixel can be analyzed without reference to another pixel, or a reference sample. Most thermography methods are based on identifying contrast between a pixel and its neighboring pixels (i.e. a defect free pixel on the sample or an external reference sample) because a single pixel time history, when viewed in isolation, has little meaning. The TSR method was developed to exploit the sensitivity of the logarithmic derivative signal, in order to create subsurface images that provide considerably more detail and depth range than conventional contrast-based results.

Now referring to FIGS. 2A-2F, a natural log(ln) plot (FIG. 2A), a $1^{st}$ derivative plot (FIG. 2B), and a $2^{nd}$ derivative plot (FIG. 2C) of two thermographic signals 210', 212' are graphically shown. Signals 210' and 212' are taken from locations 210, 212 respectively of a surface of sample 10a, 10b. Location 212 represents a portion of a sample 10a that is defect free and location 210 represents a portion of sample 10b that includes a sub-surface defect. By observing and comparing (at time=ln($t_x$)) thermographic signal reconstruction (TSR) images 202, 204, 206 each of which correlates to a natural log (ln) plot 102, a 1$^{st}$ derivative plot 104, and a 2$^{nd}$ derivative plot 106, respectively, it is readily visible that certain characteristics of the logarithmic 2$^{nd}$ derivative signal plot 106 are extremely beneficial for understanding one or more characteristics or subsurface states of a sample 10a, 10b. Specifically, the behavior of the 2$^{nd}$ derivative plot 106 is largely independent of: (a) the amount of heat (i.e. energy pulse 14 shown in FIGS. 3 and 5) used to excite the slab sample 10a, 10b; (b) the composition of the material comprising sample 10a, 10b; or (c) the type of infrared camera 16 (FIGS. 3 and 5) used to detect the emitted heat (energy) 18. Although the time and amplitude of the defect peak 210 will shift according to the depth at which an interface is encountered, or the composition of the host material or defect, the basic shape characteristics of the peak will remain unchanged and readily distinguishable from the defect-free signal 212, which has negligible amplitude. Furthermore, the processing analysis using a 2$^{nd}$ derivative plot 106 can be easily automated (no operator discretion is necessary) and it is directly applicable to various heating techniques including: (a) an instantaneous pulse, (b) an extended pulse (step heating or the subsequent cooling), (c) continuous heating, or (d) modulated heating or cooling.

The 2$^{nd}$ derivative also reduces the influence of undesirable artifacts that typically occur when samples with low-emissivity surfaces are inspected. These artifacts include narcissus (where the IR detector sees its own reflection from the sample surface), and reflection of background IR radiation off of the sample surface and into the camera. For many materials, the temporal behavior of these artifacts is essentially static or slow over the time scale during which the derivative peak occurs. In such cases, the derivative images appear to be artifact-free, while the corresponding original temperature images may be completely corrupted by artifacts.

Many of the existing approaches for analyzing thermographic data include comparing a defect-free sample 10a against a defective sample 10b. In these contrast-based approaches, it is impossible to interpret a single pixel time-history without utilizing some reference for comparison or correlation. Although these methods may be quite mathematically sophisticated (e.g. principal component analysis, pulse phase thermography or lock-in detection), definitive interpretation inevitably requires the use of a defect-free reference sample 10a. Furthermore, contrast based methods are extremely difficult to interpret in cases where a sample is entirely good or bad, since either case does not generate significant contrast. The present invention is not a contrast method, and allows for interpretation of a single pixel time history without a reference sample or a priori information. In an embodiment, the present method 100 takes advantage of invariant properties of heat conduction in a solid sample 10a, 10b, so that results for each pixel can be expressed as a set of numbers that have explicit physical meaning (as opposed to relative values associated with contrast methods).

Figure 3:
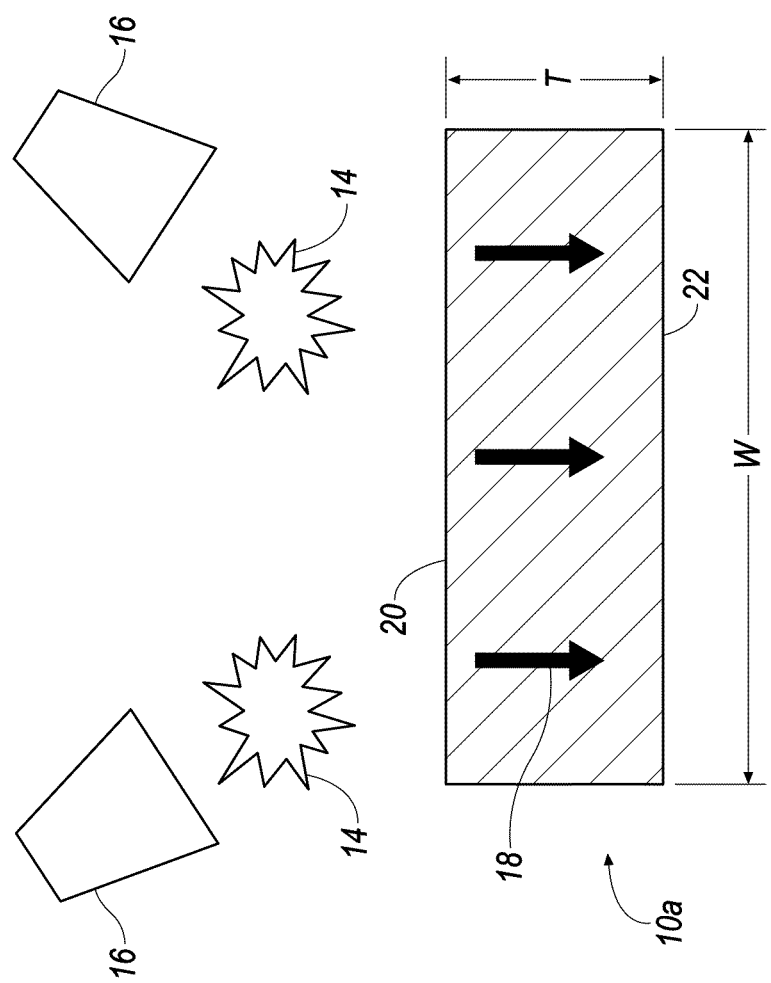
FIG. 3 is a representative diagram of a thermographic imaging system heating a test sample that is free of internal defects.
Figure 4:
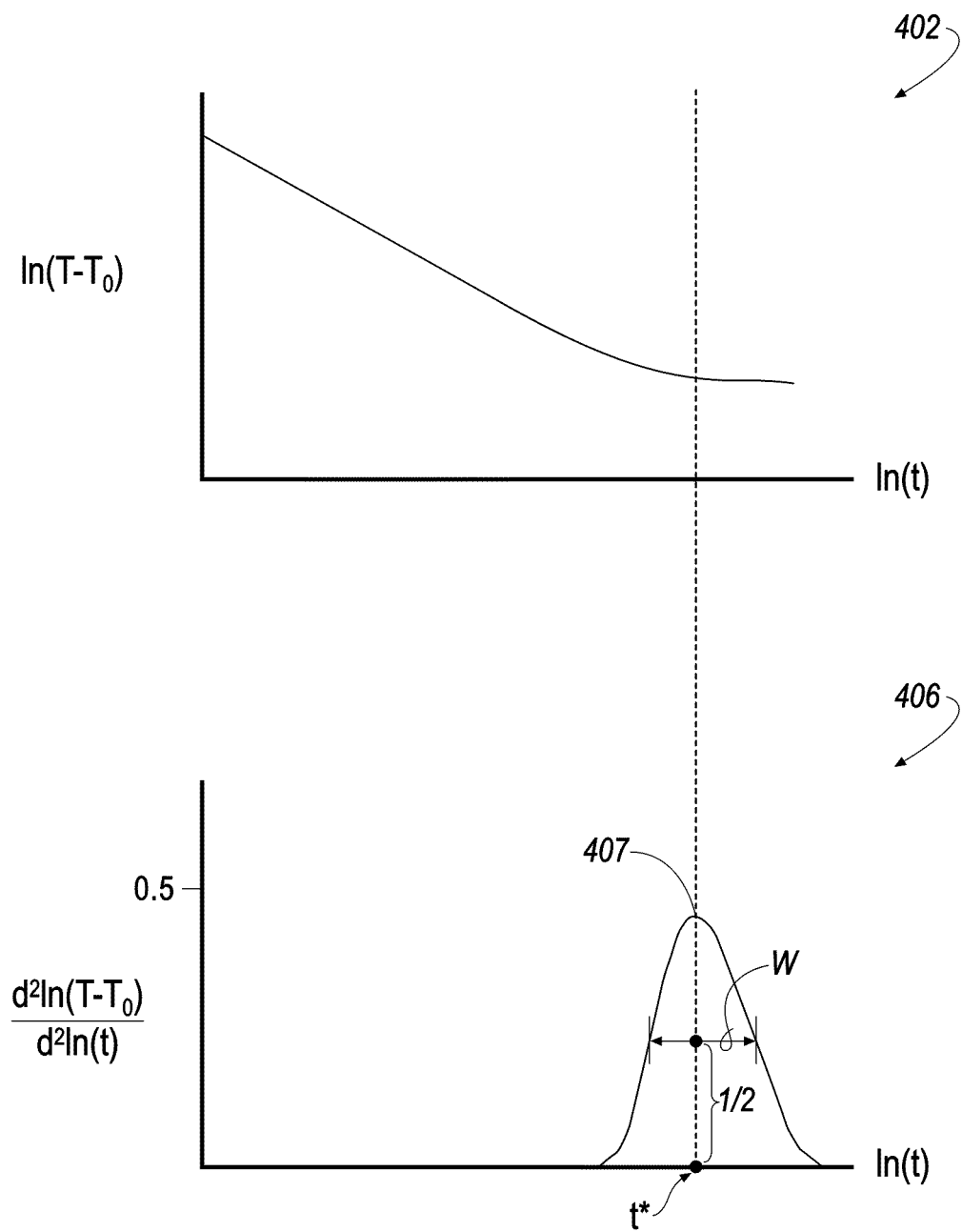
FIG. 4 illustrates a natural log(ln) plot and a $2^{nd}$ derivative plot of TSR defect detection obtained from an ideal slab the sample of FIG. 3 according to an embodiment.

Referring to FIGS. 3 and 4, a natural log(ln) plot 402 and a 2$^{nd}$ derivative plot 406 resulting from a uniform heat pulse 14 applied to a front surface 20 of the defect-free slab sample of material 10a is shown according to an embodiment. Referring to Equation 1 below, a solution for the temperature of the front surface 20 can be expressed in a series as follows:

$$T(t) = \frac{Q}{kL}\left[\alpha t + 2\sum_{m=1}^{\infty}\frac{1}{\beta_m^2}(1 - e^{-\alpha\beta_m^2 t})\right] \quad (1)$$

where:

T=temperature of sample surface
t=time
Q=input energy flux,
k=thermal conductivity,
α=thermal diffusivity,
L=sample thickness, and $$\beta_m = \frac{m\pi}{L}, \text{ where } m = 0, 1, 2 \ldots$$

As illustrated, the 2$^{nd}$ derivative plot 406 includes a single peak 407 occurring at a time, t*, that plot can be approximated by a Gaussian function as follows:

$$\frac{d^2 \ln(T)}{d \ln(t)^2} = 0.47 e^{-\left[\frac{\ln(t) - \ln(t^*)}{.594}\right]^2} \quad (2)$$

where:
T=temperature
t*=time at which the peak occurs,
A=amplitude of the peak, and
W=width of the peak.

The presence of peak 407 indicates that heat 18 from the applied heat pulse 14 has reached the back wall 22 of the sample 10a, and that normal one-dimensional diffusion of heat 18 from the front surface 20 has been interrupted (by reaching the back wall 22).

The time at which the peak 407 occurs can be correlated to the thickness of the sample 10a using the relationship $$L = \sqrt{\alpha \pi t^*}$$

where:
L=thickness of sample,
α=thermal diffusivity of the sample, and
t*=time at which the 2$^{nd}$ derivative peak occurs.

In the ideal case, where no heat is transferred from the back wall of the sample to the surroundings, the 2$^{nd}$ derivative amplitude reaches a maximum possible value of 0.47.

The width W (i.e., full width at half maximum) of the peak 407 for the adiabatic sample 10a remains invariant with a value of 0.47, regardless of the thickness, L, of sample 10a. The width W of the peak 407 represents: (a) the time interval between heat 18 from the heat pulse 14 first arriving at the back wall 22 of the sample 10a, and (b) the back wall 10a reaching its maximum temperature. In the ideal slab case, the ratio of these times is fixed at 0.594, and independent of the thermophysical properties of the host material.

Figure 6:
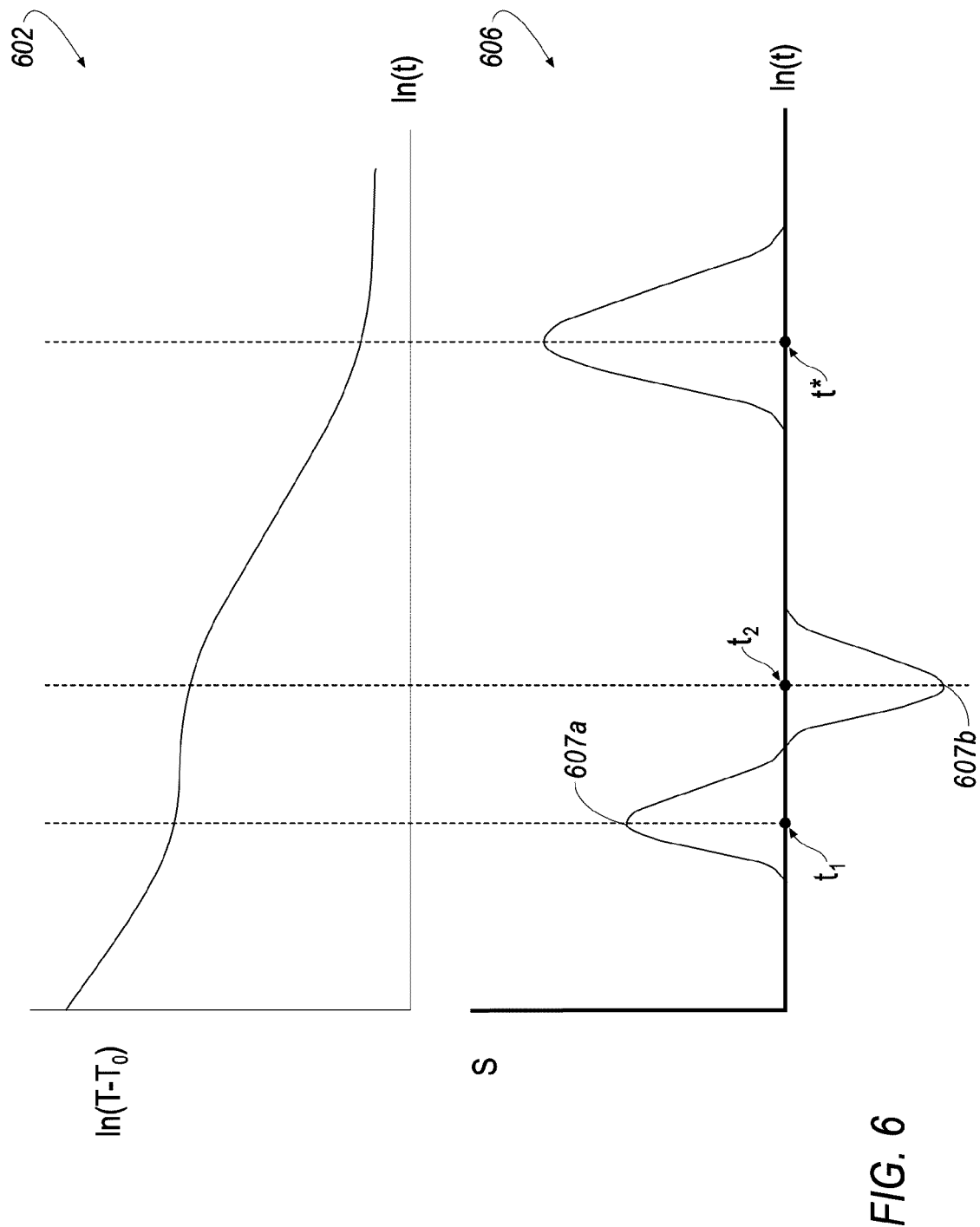
FIG. 6 is a graph of natural log(ln) plot and a $2^{nd}$ derivative plot of TSR defect detection obtained from the sample of FIG. 5 according to an embodiment.

Referring now to FIGS. 5 and 6, a natural log(ln) plot 602 and a 2$^{nd}$ derivative plot 606 resulting from a uniform heat pulse 14 applied to a front surface 20 of a sample of material 10b including a defect 12 is shown according to an embodiment. For points on the surface located away from the defect 12, the 2$^{nd}$ derivative signal 606 will be substantially identical to the defect free 2$^{nd}$ derivative signal 406. However, for points located proximate subsurface defect 12, the 2$^{nd}$ derivative plot 606 will comprise at least two peaks of opposite polarity, which are shown generally at 607a, 607b according to an embodiment.

The first peak 607a in the 2$^{nd}$ derivative plot 606 occurs at a time, $t_1$, and can be correlated to the arrival of heat 18 from the surface at the interface of the defect 12. The second peak 607b occurs at a time, $t_2$, and can be correlated to the lateral flow of heat 18 off of the defect 12. The timing of the first peak 607a is dependent on the thickness/depth of the defect 12, while the timing of the second peak 607b is dependent on the width/diameter of the defect 12.

Thus, in the exemplary case, a pixel from a TSR image data set defect-free slab will exhibit an all-positive (peak 407) $2^{nd}$ derivative signal 406 whereas a defective pixel will have both positive and negative peaks 607a, 607b. It is a simple matter to distinguish between defective and non-defective pixels by considering the polarity of the 2nd derivative signals 406, 606. No reference sample is needed to make this distinction between a defective or intact point on the sample. In fact, a filter (not shown) may be applied to the data to provide a binary image (see 900b of FIG. 9), so that, for example, a value of "1" could be assigned to pixels with a negative going peak (e.g., peak 607b), and value of "0" could be assigned to pixels with a positive going peak (e.g., peak 607a).

The present invention can also be used for the purpose of quality assurance in manufacturing, where no specific defect or characteristic is necessarily detected or measured. Instead, the process serves to verify that the sample under consideration is fundamentally identical to a master sample that has independently been determined to be acceptable. Verification is accomplished by comparison of the $2^{nd}$ derivative curve of the test sample with that of the master sample.

In commercial applications, samples are subject to influences from their surroundings, and internal defects 12 or a back wall interface may only partially obstruct the flow of heat 18. Equation 2 provides a limiting case as it represents an ideal (adiabatically isolated) interface which does not allow heat to pass through the back wall of the sample. A real interface will allow some heat to pass, and will act to decrease the amplitude and width of the positive and negative peaks 607a, 607b from the maximum values observed in the adiabatic case. However, the basic uni-polar/bi-polar behavior of the $2^{nd}$ derivative is preserved in the presence of a real interface, which can prove useful when combined with one or more binary/classification operations including for example: (a) detecting the occurrence of a 2nd derivative peak 607a, 607b of specified polarity in a specified time window, (b) detecting the occurrence of a zero-crossing of the derivative signal 606 in either a positive or negative-going direction in a given time window, (c) detecting the occurrence of a derivative peak value greater (or less than) a given threshold value, (d) detecting the correlation of a peak 607a, 607b to a Gaussian shape with specified with and amplitude characteristics to within a specified tolerance (e) detecting the correlation of a peak 607a, 607b to the $2^{nd}$ derivative peak of a master sample (i.e. sample known to be good) to within a specified tolerance or (f) detecting the occurrence of a fractional value of the peak amplitude in a specified time window immediately preceding or following the peak (e.g. the time at which the full width half maximum value of the peak occurs).

Figure 7:
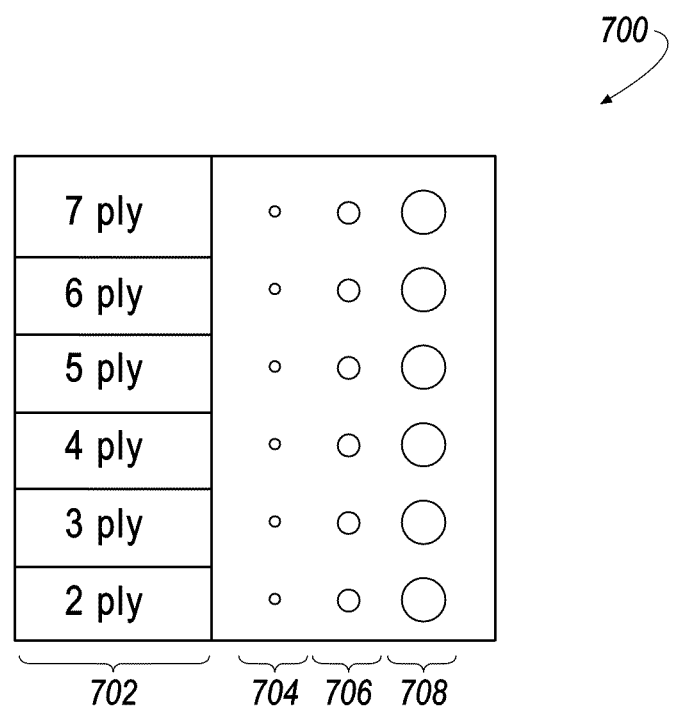
FIG. 7 is a diagrammatic view of a test sample including a plurality of ply layer steps 702 and defect inserts 704, 706, 708 of varying diameter according to an embodiment.
Figure 8:
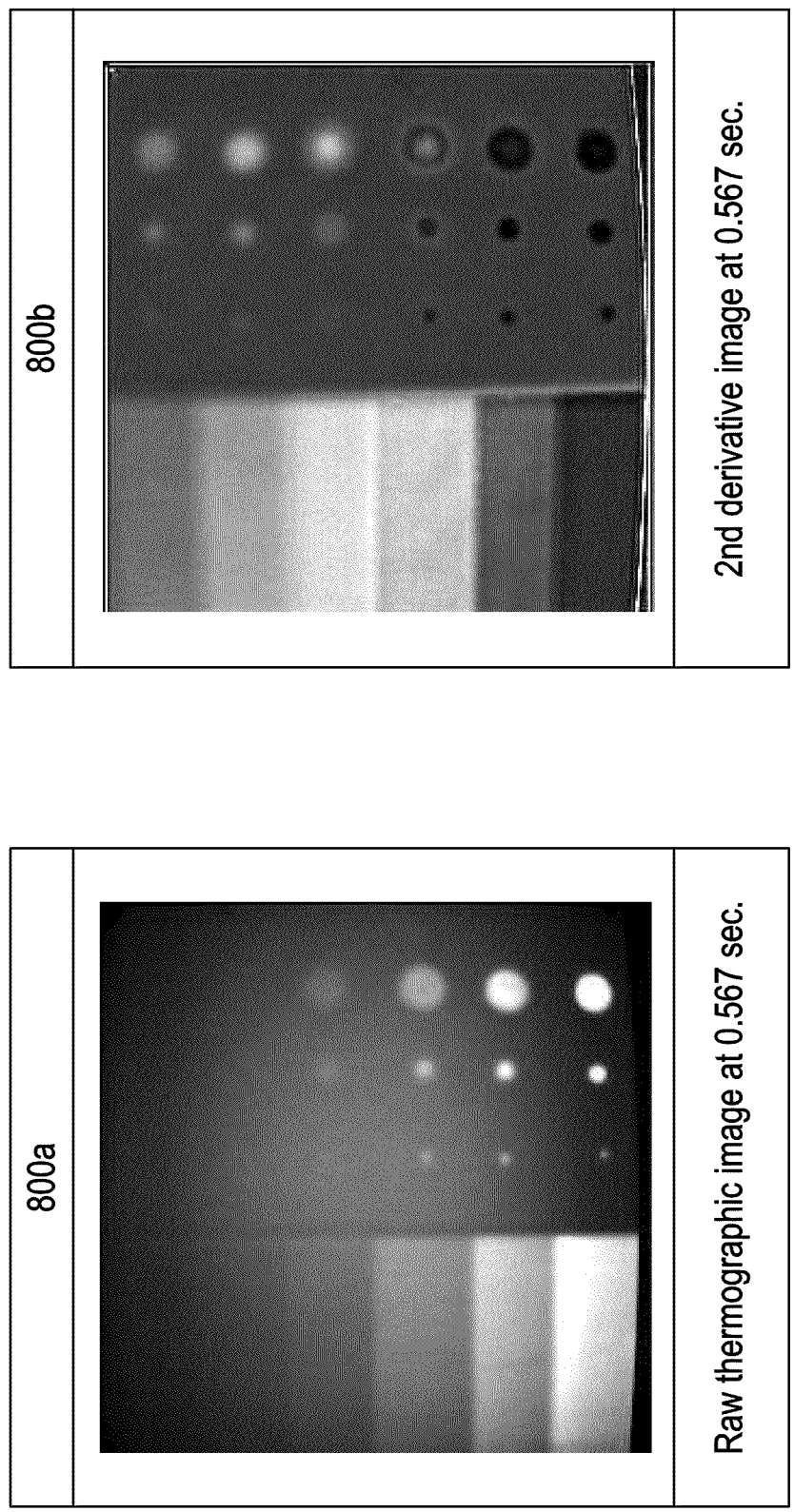
FIG. 8 is a raw thermographic image (800a) taken at 0.567 seconds after illumination and a $2^{nd}$ derivative image (800b) of the test sample of FIG. 7 taken at 0.567 seconds after illumination according to an embodiment.

In relation to the following description associated with FIGS. 7 and 8, a diagrammatic view of the composite laminate test sample is shown in FIG. 7. Unprocessed 800a and $2^{nd}$ derivative 800b thermographic images of test sample 700 are shown in FIG. 8. Vignetting artifacts due to improper camera calibration appear in the unprocessed image (800a), but are removed in the derivative image (800b). Sample 700 generally includes a series of "n-ply layer" steps 702, and implanted discrete internal defects 704-708, placed between various ply layers. The series of n-ply layer steps 702 include, as illustrated, 2-, 3-, 4-, 5-, 6-, and 7-layer steps. The discrete defects 704, 706 and 708 are approximately, 0.25", 0.5" and 1" in diameter, respectively. Smaller, deeper features, i.e. those with the smallest diameter to depth ratio, are difficult to detect in the unprocessed thermographic image 800, but they are detectable in the derivative image (compare 800a against 800b).

Figure 2:
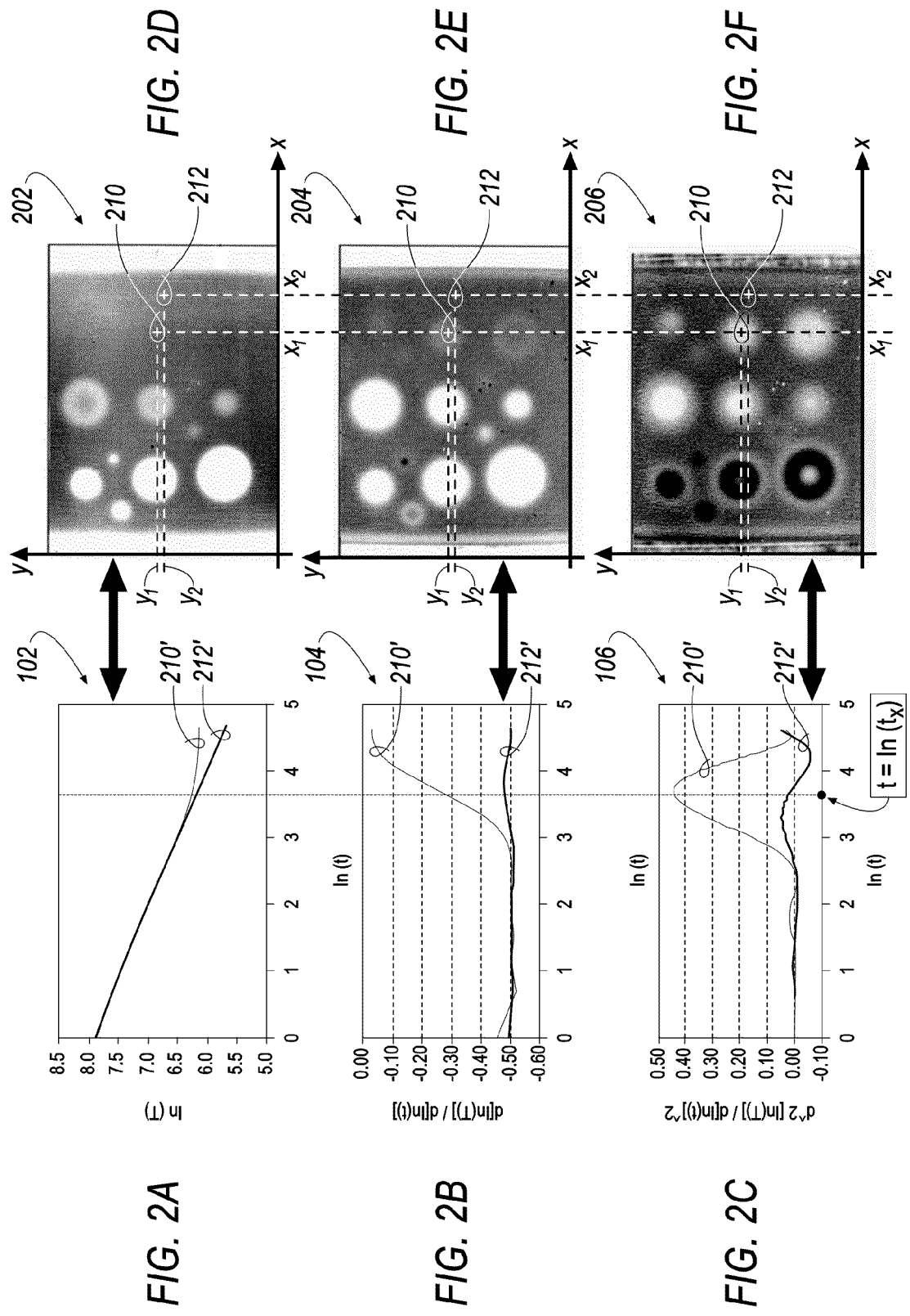
FIGS. 2A-2C illustrate natural log(ln) versus time plot, a $1^{st}$ derivative versus time plot, and a $2^{nd}$ derivative versus time plot of two locations of a sample using a thermographic signal reconstruction (TSR) defect detection according to an embodiment.
FIGS. 2D-2F are entire sample images constructed from digital thermographic data captured at time $t_x$ and processed using natural log versus time, $1^{st}$ derivative versus time, and $2^{nd}$ derivative versus time transforms.
Figure 9:
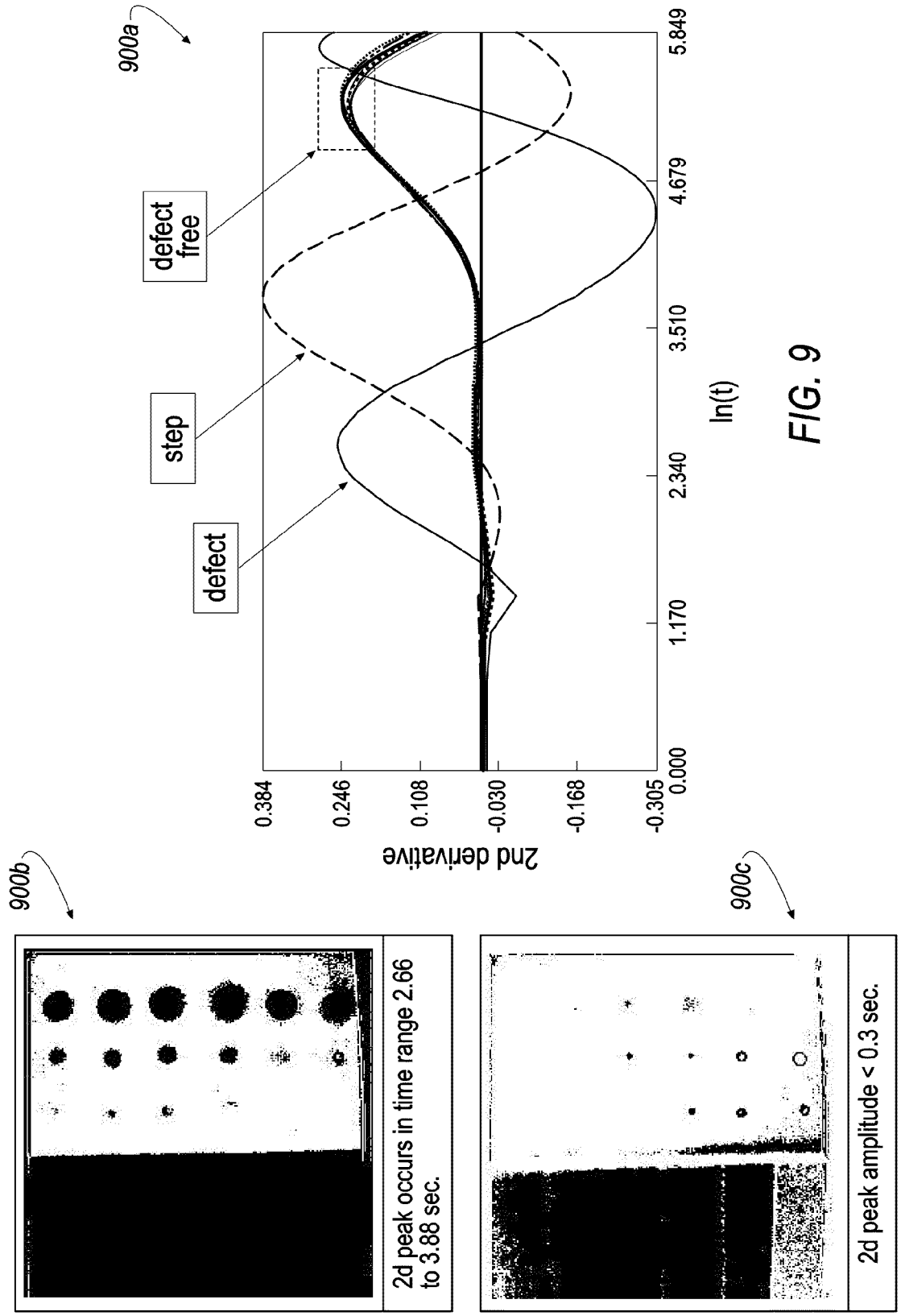
FIG. 9 shows one $2^{nd}$ derivative logarithmic plot and two $2^{nd}$ derivative images that have been generated using various binary classification operations.

Referring now to FIGS. 1 and 9, the novel method 100 may be carried out by utilizing characteristics of the logarithmic $2^{nd}$ derivative plot 900a to create $2^{nd}$ derivative binary images as shown generally at 900b and 900c. As such, steps S.101-S.103 may include: (a) thermally disturbing a sample and collecting thermal data (over a period of time), (b) creating a natural log(ln) transformation of the collected data (as a function of time), (c) converting the thermal data using a $2^{nd}$ derivative function as shown in FIGS. 2 and 5-6, (d) binarizing (i.e. applying one or more binary classification operations) the $2^{nd}$ derivative curve for each pixel based on a condition such as the time or amplitude of the derivative peak, zero crossing, peak width, polarity of the peak or asymptotic value of the curve, etc. Applying one or more binary conditions to the data sequence yields a binary image 900b and 900c that indicates pixels that meet the condition as TRUE (white in the examples provided). As such, the white pixels in image 900b indicate all pixels where the $2^{nd}$ derivative peak occurs in the time window 2.66 sec to 3.88 sec. Similarly, white pixels in image 900c indicate all pixels where the $2^{nd}$ derivative peak amplitude is less than 0.32 sec.

Figure 10:
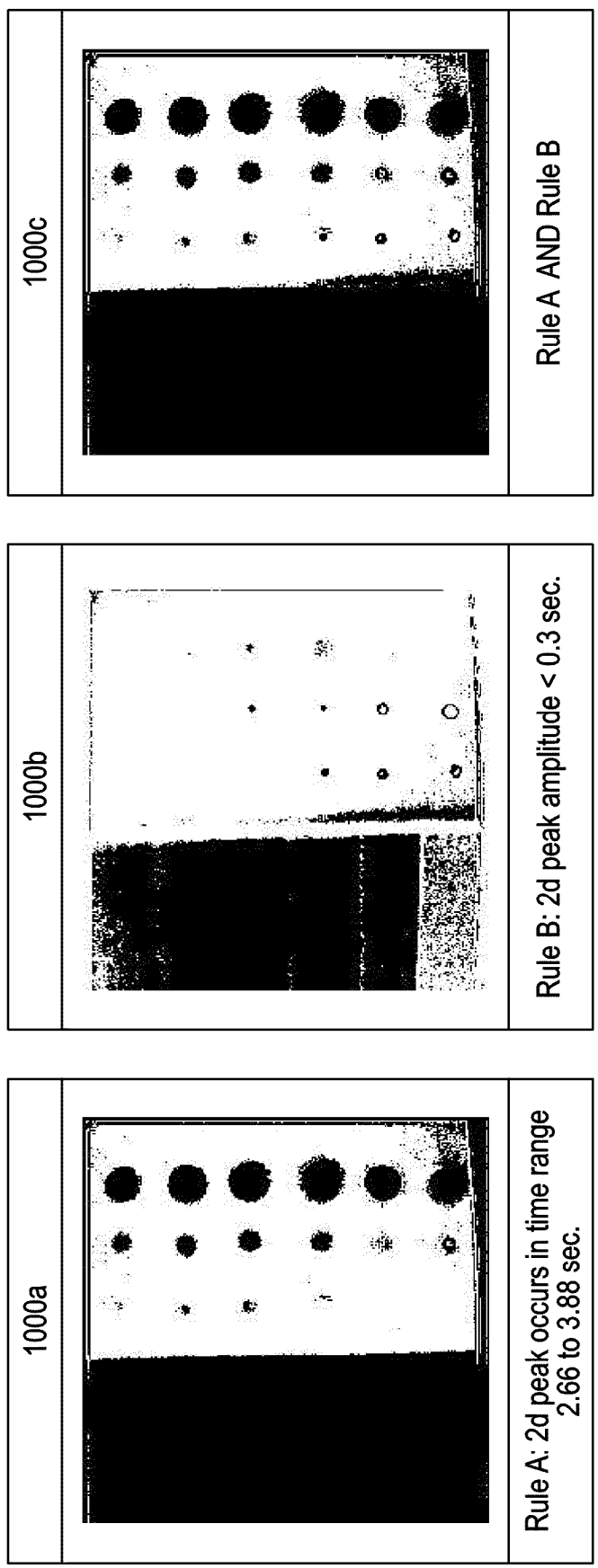
FIG. 10 includes two $2^{nd}$ derivative binary images that are combined using a Boolean AND operation.

Then, as shown in step S.104 and in FIG. 10, an image 1000c may be obtained by performing a Boolean operation on multiple instances of the $2^{nd}$ derivative converted data, which may be data that gives rise to the images 900b and 900c. According to the illustrated embodiment, the image 1000c is a Boolean AND operation on the images 900b and 900c (images 900b and 900c have been reproduced as 1000a and 1000b respectively). As such, the image 1000c may be referred to as a $2^{nd}$ derivative Boolean image of the binary images 900b and 900c According to the illustrated embodiment, the image 1000c is the logical AND of the images 900b and 900c, however, it will be appreciated that the logical Boolean operation used to generate image 1000c is not limited to a single operation, such as those set forth in the present example. Alternatively, the image 1000c may be generated by a serial or parallel sequence of operations, or, as a group of nested operations, such as, for example, logical operations including one or more of an "AND," "OR," or "NOT" function. Accordingly, the binary operations can be quickly carried out once the $2^{nd}$ derivative has been calculated in step S.103, and, as such, can be used with TSR processed data.

As shown in FIG. 9, meeting a single logical condition may be a necessary, but not sufficient, condition for a pixel to be characterized as defective, intact or otherwise. However, each applied binary condition identifies pixels that meet a single condition and discards all others in step S.105. The method 100 is then advanced to step S.106 where Boolean-operations are performed on data of the binary images 900b and 900c, resulting in defect map image 1000c at step S.107. The defect map image 1000c utilizes the data provided in all input binary images so as to point out defects that may not have been detected in one or more of the images 900b and 900c. For example, neither image 900b nor 900c detected all of the defects that are made manifest in Boolean image 1000c. Accordingly, the defect map image 1000c, when considering the data provided by the images 900b and 900c, or any single thermographic image such as 800a, illustrates the presence of all defects when other images indicated that no such defects exist.

It will also be appreciated that binary operations may be performed on raw, logarithmic (ln), or logarithmic 1st derivative data. However, it has been found that the 2nd logarithmic derivative is particularly well-suited to binary processing since the behavior of the 2nd derivative is not affected by: (a) the amplitude or distribution of input heat (energy pulse) 14, (b) the ambient conditions, or even (c) the camera 16 used to acquire the data (which may not be necessarily true of the raw data that is highly sensitive to all factors described above).

Additionally, the method 100 could be applied to samples that have been heated by a pulse 14 from a constant or modulated heat source. As the width of the pulse 14 increases beyond the instantaneous case, the pulse 14 can be treated as a step, and the response of the sample can either be viewed while the pulse is active (i.e., energy is being applied to the front surface 20) or after the pulse 14 has been deactivate. Immediately after the pulse 14 is deactivated, the sample cools monotonically, but there is an initial time interval during which the derivative behavior deviates from the instantaneous case. However, after that initial time interval has lapsed, the $2^{nd}$ derivative results for the pulse and the step case is identical (i.e., typically, the step approach is used for thicker samples, where the "settling time" of the derivative is small as compared to the transit time through the sample).

During the heating period, however, while the pulse 14 is active, the sample surface temperature rises monotonically. As in the instantaneous heating case, the logarithmic $2^{nd}$ derivative displays a positive peak that corresponds to the back wall interface. The shape of the peak is asymmetric, but the peak time depends of the thickness or composition of the sample. As in the case of the instantaneous pulse 14, the amplitude and width of the peak in the adiabatic case are the maximum possible values. The width and amplitude will vary predictably as the $2^{nd}$ layer material varies. Furthermore, the presence of a subsurface defect 12 will result in a bipolar peak in the logarithmic $2^{nd}$ derivative.

In certain cases (e.g. materials with low infrared emissivity, or, small portable inspection systems where the heat source and camera 16 are in close proximity to the sample and/or each other), it may be desirable to modulate the heat source. The motivation for this is to eliminate undesirable secondary infrared signal components that are generated by heat source hardware that becomes heated while the pulse is active. Heated hardware or background will emit IR energy that may be reflected into the camera from the sample surface 20 or background. These reflected signals can overwhelm or mask the emitted infrared signals that emanate from the sample surface 20 and therefore interfere with data interpretation or measurement. It is important to note that the modulation scheme described herein does not involve "thermal wavelengths" (TW) or any kind of resonant scheme (RS) where the modulation frequency is chosen to match material properties and thickness/depth. In the present invention, the frequency is intentionally chosen to be higher than frequencies traditionally employed in the TW/RS approaches. The disclosed approach uses relatively high frequency excitation as a carrier for the emitted signal. The emitted signal is then used to construct a monotonically increasing signal based on the steady state heating component of the modulated component.

Now referring to FIG. 11, in an embodiment of a modulated heating scheme, a heat source maybe activated and deactivated with a set periodicity. For example, a square wave modulation scheme may be used such that the resulting sample surface temperature can be described as a "rising saw tooth" (see FIG. 11A) where each "tooth" is asymmetrical. During the rising portion $t_1$, the heat source is active and the infrared camera 16 detects both emitted and reflected radiation. However, during the falling portion $t_2$, the camera 16 detects only radiation that is emitted from the sample surface 20. In an embodiment of the present method, the falling portions of the saw tooth signal may be utilized so that the temperature vs. time plot for a single pixel is a piecewise continuous function. FIG. 11A is a plot of the surface temperature versus time for a slab sample being heated by a modulated heat source. The modulation scheme used to create the plot of FIG. 11A includes operating the heat source at a 50% duty cycle including one second heating and one second of cooling at a heat density of 1500 Watts/meter$^2$ The rising portion of each saw tooth (i.e. $t_1$) represents the time where the heat source is active and the falling portion of each saw tooth (i.e. $t_2$) represents the portion of the saw tooth where the source is inactive. FIG. 11B represents a monotonically ascending function that is creating by sampling a point during each saw tooth's inactive cycle (i.e. $t_2$) that has the same time delay after the heating source is inactivated. Each discrete point from each saw tooth is used to create a continuous function using TSR (i.e. low order polynomial fit). FIGS. 11C and 11D are first and second derivatives of the function shown in FIG. 11B. Although the shape of the second derivative is not identical to the pulse heating embodiment described earlier, it behaves in a similar manner to that which has already been described in terms of peak response to an interface, polarity, etc. and, therefore, it can serve as a basis for automated binary processing.

The driving function which describes the modulated heat function used to generate the saw tooth profile of FIG. 11A:

$$f(t) = \begin{cases} Q & \text{for} - \text{all} - t_1 \leq t \leq t_{1'}, t_2 \leq t \leq t_{2'} \ldots t_n \leq t \leq t_{n'} \\ Q = 0 & \text{otherwise} \end{cases} \quad (3)$$

The solution to the one dimensional heat equation during the cooling times of a modulated heating cycle is shown below:

$$T(0, T \in \text{Cooling time after } t_n, \text{ before } t_{n+1}) \quad (4)$$

$$T = \frac{Q}{kL} \sum_{i=1}^{n} \left[ (t_i - t_i)\alpha + 2 \sum_{m=1}^{\infty} \frac{1}{\beta_m^2} (e^{\alpha \beta_m^1 (t_i - t)} - e^{-\alpha \beta_m^2 (t_i - t)}) \right]$$

$$\beta_m = \frac{m\pi}{L}$$

$$m = 0, 1, 2, \ldots$$

wherein:
T=surface temperature of sample
$t_i$=beginning time of the i$^{th}$ heat pulse delivered by the heat source
$t_i$=the n time of the i$^{th}$ heat pulse delivered by the heat source
L=thickness of sample
α=thermal diffusivity of the sample A nonlinear, least-squares fit of the piecewise continuous function using a low-order polynomial and a truncated Fourier series (typically 5-terms or less is sufficient) may be utilized. The Fourier series represents the modulated carrier, and the polynomial represents the emitted radiation from the sample surface 20 due to a constant flux heat source. Effectively, a TSR may be performed on the steady state component of the modulated signal. As such, one may analyze the logarithmic derivatives of a sample, as described above.

The same result may be achieved more simply by sampling a point from the falling signal of each period, where each point has the identical time interval with respect to the cessation of the heating signal. These points can be used to create the piecewise function, and fit with a low-order polynomial (the Fourier series is not necessary in this embodiment).

It will be appreciated that one may apply the same automated analysis tools, based on the behavior of the logarithmic $2^{nd}$ derivative, the rising surface temperature, the falling surface temperature, or the modulated surface temperature. Analysis of each pixel may be a single logical operation, a combination of operations, or, a nested or conditional sequence of operations. Some examples are presented in Table 1 as follows:

TABLE 1

| TASK | OPERATION |
|---|---|
| Identify discrete defects (e.g. voids) in a plate | Find all pixels with positive $2^{nd}$ derivative peak followed by a negative $2^{nd}$ derivative peak. |
| Identify discrete defects in a defined depth range | Find all pixels with positive $2^{nd}$ derivative peak followed by a negative $2^{nd}$ derivative peak where the positive peak is in a specified time range. |
| Confirm sample is substantially similar to specification (gold standard sample) | Find all pixels with $2^{nd}$ derivative peak time, peak time amplitude, and zero crossing time (if any) behavior that matches a gold standard (i.e. a defect free sample). |
| Identify sample areas that do not match specification | Find all pixels that do not have $2^{nd}$ derivative peak time and amplitude and width and zero crossing (if any) behavior that matches the gold standard. |
| Detect anomalous boundary conditions on sample back wall (foreign material, anomalous bonding or convective cooling variations) | Identify pixels where the post-peak $2^{nd}$ derivative goes asymptotically negative. |
| Detect inclusion or thermally conductive substrate | Find all pixels with only a negative peak. |

Using the derivative analysis method as described here, it is possible to detect or measure some sample characteristics that could not be accomplished by other thermographic approaches. One such example involves mapping of the heat transfer coefficient variations on the back wall 22 of a sample 10a, 10b. To do this, a steady convective fluid flow is established at the back wall 22 and the sample 10a, 10b is allowed to reach an equilibrium state with the fluid flow. Once equilibrium has been reached, the front surface 20 of the sample 10a, 10b is heated using one of the methods described above, and the logarithmic $2^{nd}$ derivative is computed using TSR or some other means. The resulting derivative signal is identical to the adiabatic case, except that after the peak corresponding to the back wall interface has subsided, the signal goes negative, and (unlike a discrete defect signal) does not return to a positive value.

It is conceivable that one could claim that existing methods of analyzing thermographic data could be adapted to automated binary processing. However, such an adaptation would require either an unrealistic degree of control of experimental parameters (for the typical inspection or manufacturing environment), or a priori knowledge of the thermophysical properties of the sample. For example, one could use well-known methods to ascertain the state of a sample by direct measurement of the surface temperature with the IR camera, so that pixels outside of a specified temperature range would be deemed as indications of a subsurface defect. However, in attempting to automate and binarize such an approach, it must be recognized that there are numerous mechanisms other than subsurface features that are capable of generating an anomalous surface temperature response. These include ambient temperature, surface emissivity variations (possibly due to dirt, grease, or perhaps a paint variant or a decal), input energy variations (e.g. due to lamp or power supply variations aging or ambient temperature conditions), IR camera calibration or position, or reflection artifacts. In order to overcome these factors to facilitate automation and binary processing, it would be necessary to establish a new defect criteria daily, or even hourly to accommodate changing conditions in the inspection environment. The present invention has a high degree of immunity to all of the issues described above, so that frequent calibration is eliminated.

Similarly, one could employ known methods that apply advanced mathematical processing to the surface temperature data, and attempt to automate and binarize the interpretation process. As we have stated previously, in most cases these methods are fundamentally based on contrast, and require reference to a defect free sample or point. Furthermore, many of these methods are based on the correlation of surface temperature response data to a mathematical model that requires a priori knowledge of sample thermophysical properties, e.g. thermal conductivity, heat capacity, density and thickness. Furthermore, these methods are often sensitive to a particular type of defect or feature, e.g. thermal diffusivity, sample thickness or defect depth, and they may miss features that do not display features that present differences in that particular characteristic. For example, plate sample with a small adhesive bond variation at the back wall will appear as a plate with uniform thickness and diffusivity (it will appear as a change in $2^{nd}$ derivative amplitude in the present invention). The present invention is unique in that it allows one to ascertain the subsurface condition of a sample from analysis of a single pixel time history, without a priori knowledge of thermophysical properties of the sample, calibration (beyond insuring that the camera and heating equipment is in proper working order) or reference to other points or samples. In fact, the invention could be implemented without an IR camera as a single point analysis tool, using a single point temperature detector, e.g. a thermocouple.

We have described the presentation using the case of a defect or interface that is less thermally conductive than the host material, in which case a positive $2^{nd}$ derivative peak obtains. In the case of a defect (e.g. an inclusion) or interface that is more thermally conductive than the host, the same steps can be applied, with the understanding that the peak behavior we have described will be shifted by 180 degrees (i.e. a negative peak will occur at an interface, followed by a positive peak for a discrete defect).

The exemplary embodiments presented herein have included the option of utilizing binary processing of surface temperature sequence data based on the analysis of logarithmic derivatives of one or more point locations on the specimen surface (i.e. each location is represented by the time history of one or more pixels as captured by a digital IR camera.) This approach offers significant advantages compared to conventional methods that require measurement of temperature or temperature contrast, because the surface temperature of a specimen may vary on a day-to-day or even a specimen-to-specimen basis depending on factors including ambient temperature, excitation intensity, surface finish, or camera calibration. However, the derivative approach disclosed herein is largely unaffected by these factors so that the behavior of a pixel can be reliably reduced to a few relevant numerical parameters which can be, in turn, measured and used (as the basis for a binary processing scheme using subsequent Boolean operations) for robust automated defect detection and quality assurance.

The derivative characteristics identified herein, which are useful classifiers for binary processing, include various maxima, minima, and threshold crossings of the $1^{st}$ and $2^{nd}$ logarithmic derivatives and the timing associated with these crossing events. In an embodiment, the present invention utilizes the characteristics associated with the derivative peak associated with a thermal signature of a specimen having subsurface flaws, in that subsurface flaws will display thermal signature with substantially different peak behavior in terms of derivative peak time and amplitude. While this approach is quite effective at identifying discrete subsurface flaws or interfaces, further improvements are disclosed herein that directly relate to quality assurance where the presence of a discrete flaw is not likely, but rather, systemic manufacturing variations must be detected that affect the overall thermal physical state throughout the whole specimen. In such cases, the peak, threshold crossing, and asymptotic derivative behavior may be unchanged from that of the designated standard.

Figure 13:
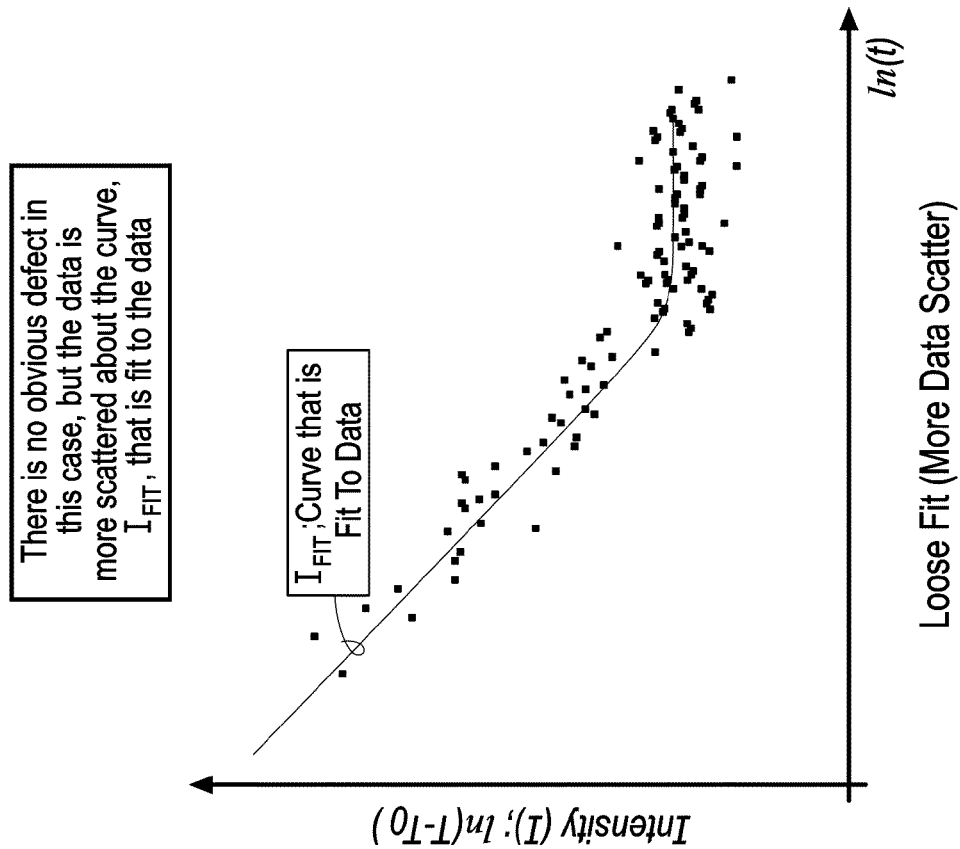
FIG. 13 is a graphical example of variance of data collected from a specimen of inferior quality to that of FIG. 12.
Figure 12:
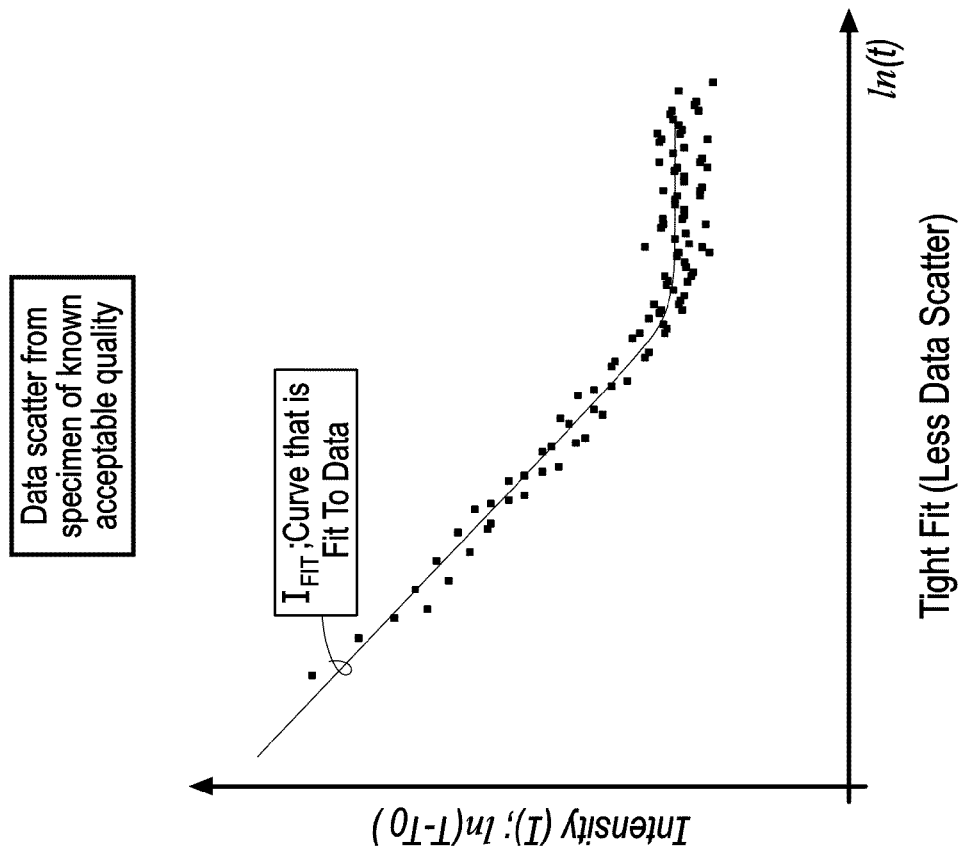
FIG. 12 is a graphical example of variance of data collected from a Gold Standard specimen.

Using the technique disclosed herein, subtle sample variations that do not rise to the level of discrete defects are rendered detectable. Examples of such subtle sample variations include distributed porosity, distributed packing density, variations in fiber composite density, and the like. An example of a non-discrete defect is discussed in conjunction with FIGS. 12 and 13. FIG. 12 sets forth a scatter plot of thermal data that is sampled, over time, from a location (x, y) on the surface of a specimen of known acceptable quality. A curve, $I_{FIT}$ is fit to the data and, because the specimen is of known acceptable quality, the variance of the various data points about the curve is relatively small. FIG. 13 can be contrasted to that of FIG. 12 wherein FIG. 13 represents the thermal scatter plot of a sample of known inferiority to that of FIG. 12. However, because the nature of the inferiority of the specimen of FIG. 13 is of the non-discrete type (e.g. distributed porosity) the characteristic curve does not exhibit some of the earmark characteristics of a defective scatter plot discussed earlier herein (such as the second derivative of the curve fit having both a positive and negative peaks). However, the degree of data scatter evidenced in the defective specimen of FIG. 13 is obviously greater than the variance for that of the sample of acceptable quality of FIG. 12. The nature of the non-discrete subsurface flaws of the specimen depicted in FIG. 13 may escape the binary processing methods described heretofore; however, the following process may be beneficial for detecting non-discrete subsurface flaws.

Figure 14:
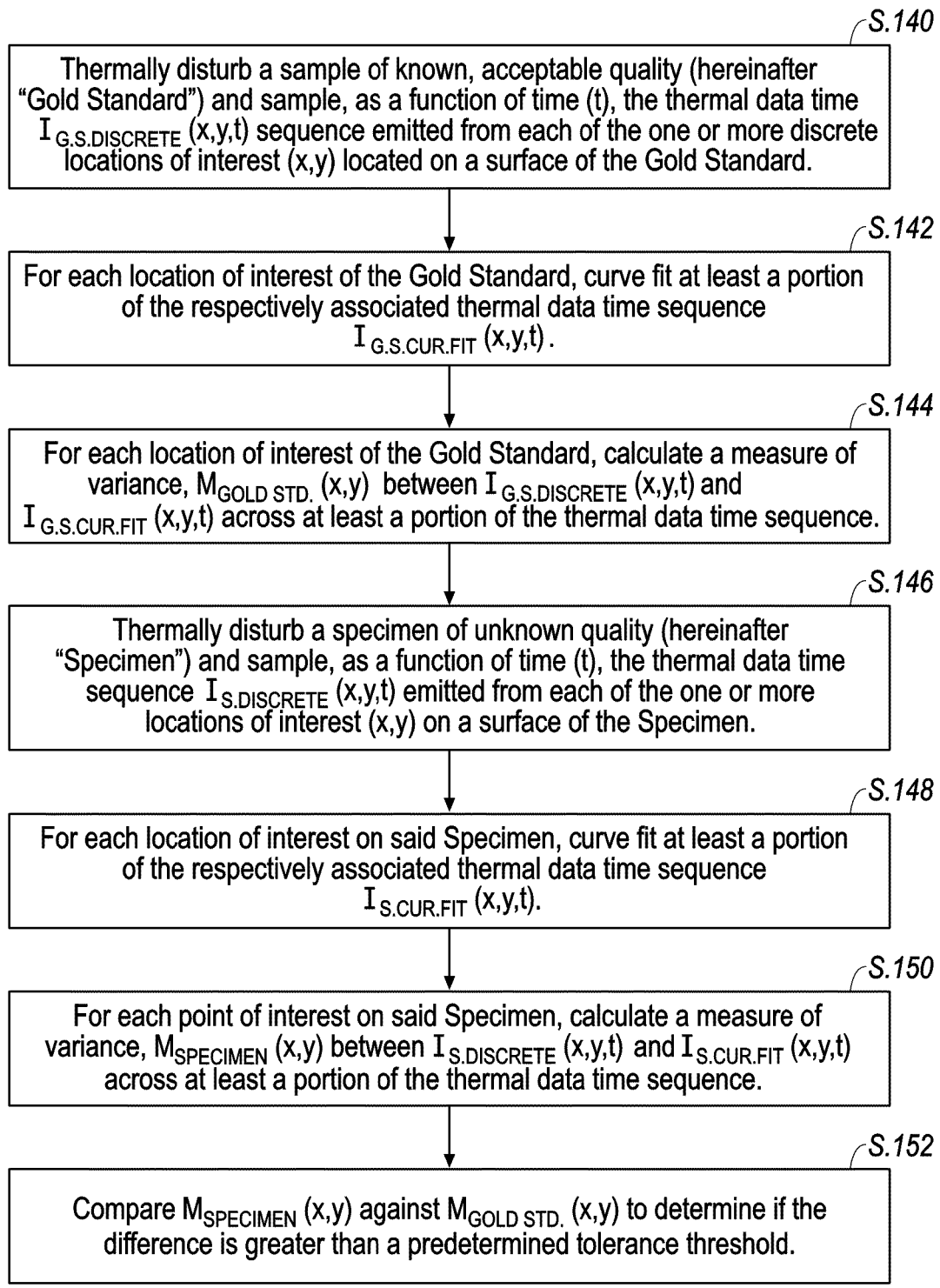
FIG. 14 is a method flow chart of an embodiment of the disclosure.

Now referring to FIG. 14, using a specimen of known acceptable quality (hereinafter "Gold Standard"), we first acquire a time varying data set using appropriate thermal excitation source and an IR camera. The thermal excitation may be instantaneous, continuous, or modulated. Also, the excitation may be represented by a heating or a cooling event. The excitation may be directed to the face of the specimen that is proximate to the IR camera or, in an alternative, the excitation may be proximate a face which is opposite to the face which is proximate to the IR camera. After the Gold Standard is thermally disturbed, the thermal data time sequence emitted from one or more discrete locations of interest (x, y) located on a surface of the Gold Standard is sampled as a function of time S.140. This sampling of thermal data is effective for extracting a monotonic data stream as a function of time. Each discrete thermal data point is a function of the location on the surface of the specimen in which it occurs (x, y) and also is a function of the time $t_j$ in which it occurs. Accordingly, $I_{G.S.DISCRETE}$ (x, y, and t).

For each location of interest (x, y) on the surface of the Gold Standard, at least a portion of the respectively associated thermal data time sequence, $t_0$ through $t_n$, is curve fit $I_{G.S.CUR.FIT}$ (x, y, and t) S.142 (see $I_{FIT}$ of FIG. 15A). Curve fitting $I_{FIT}$ may be accomplished using any number of known curve fitting techniques for creating mathematical functions having the best fit to a series of data points. Such methods include interpolation, regression analysis, piece-wise linear techniques, polynomial techniques, and the like. Also techniques known as thermographic signal reconstruction techniques (TSR) are disclosed in U.S. Pat. No. 6,751,342, which is hereby incorporated by reference. These TSR techniques may also be useful for constructing curves, or functions, which fit the discrete data.

For each location of interest S.144 on the surface of the Gold Standard, a measure of variance, $M_{GOLD\ STD.}$ (x, y), is calculated. Calculating the measure of variance associated with the $M_{GOLD\ STD.}$ (x, y), can be accomplished in any number of well-known ways such as standard deviation, coefficient of variation, or other like indicators of fit. In an embodiment, the $M_{GOLD\ STD.}$ (x, y) is calculated across at least a portion of the thermal data time sequence ($t_0$ through $t_n$). For example, if standard deviation is used to calculate variance, for each select points, $t_j$, in the data time sequence ($t_0$ through $t_n$), calculate the difference between discrete and fit measured points.

$$d_j = I_{DISCRETE}(t_j) - I_{FIT}(t_j) \quad (5)$$

Thereafter, calculate the root mean square difference for at least a portion of the thermal data time sequence as follows:

$$M = \sqrt{\sum_{j=t_o}^{t_n} d_j^2} \quad (6)$$

The result is an indicator, $M_{GOLD\ STD.}$ (x, y) of the quality of fit between the discrete data points and the curve fit to the data points. A specimen with a better fit (i.e. less variance) will have a lower M value. Ideally the M value is equal to 0 indicating that there is no variance between the discrete data points and the curve fit to the data. Presumably, the M value associated with the Gold Standard will yield the best fit results that are likely to be encountered under actual production circumstances.

Next, S.146, a thermal disturbance is applied to a specimen of unknown quality and a thermal data time sequence is captured from each one or more of the discrete locations of interest (x, y) on a surface of the specimen. The methodology set forth in S.146 precisely tracks that as disclosed and discussed with respect to S.140, the only difference is that the steps set forth in S.146 relate to a specimen of unknown quality and the steps set forth in S.140 relate to a specimen of known quality (i.e. the Gold Standard).

Next, S.148, for each point of interest on the specimen, a curve is fit to at least a portion of, the respectively associated thermal data time sequence. The steps set forth in S.148 identically track the steps sets forth in S.142, the only difference is that the steps set forth in S.148 relate to a specimen of unknown quality. The methodologies for various ways to calculate $M_{SPECIMEN}(x, y)$ are identical to those discussed in conjunction with calculating $M_{GOLD\ STD.}(x, y)$ in S.144.

Lastly, S.152, $M_{SPECIMEN}(x, y)$ is compared against $M_{GOLD\ STD.}(x, y)$ to determine if the difference is greater than a predetermined tolerance. If the difference between the two measurements of variance is less than or equal to a predetermined tolerance threshold, the specimen is considered acceptable. Likewise, if the difference between the two measures of variance exceeds the predetermined tolerance threshold, the specimen is considered suspect and appropriate measures can be taken. Various methods can be used to determine an acceptable predetermined tolerance threshold. One such approach is to statistically sample numerous specimens of known acceptable quality (i.e. numerous Gold Standard specimens). Thereafter, by measuring the statistical deviation between numerous specimens of known acceptable quality, an expected range of variance amongst specimens of acceptable quality can be determined and quantified (i.e. 1 sigma, 2 sigma, 3 sigma).

The calculation of the measure of variance allows us to reduce a time sequence of data into a single number (both for the Gold Standard and for the specimen of unknown quality). This result conveniently allows us to directly use the binary processing schemes disclosed herein.

The present invention has been particularly shown and described with reference to the foregoing embodiments, which are merely illustrative of the best mode or modes for carrying out the invention. It should be understood by those skilled in the art that various alternatives to the embodiments of the invention described herein may be employed in practicing the invention without departing from the spirit and scope of the invention. Many well-known mathematical manipulations have been discussed herein for use in conjunction with the disclosed invention. For example, the following mathematical manipulations have been disclosed herein: logarithmic conversions (including natural logs), 1st derivatives, 2nd derivatives, Fourier series, polynomial conversions, nonlinear functions, least-squares fit, piecewise functions, continuous functions, standard deviation calculations, and the like. It is to be understood that both traditional and non-traditional methods that can be used to implement these various manipulations. Also, it is recognized that there are alternative ways to carry out these manipulations which serve as approximations or proxies to the manipulations. Accordingly, the present invention contemplates both the traditional methods of implementing these manipulations and equivalent or approximate methods for carrying out these manipulations. Also, although it is believed that a digital computer provides the most efficient means of carrying out many of the methods disclosed herein in association with carrying out the present invention, nothing disclosed herein shall limit the scope of this invention to its implementation by digital computers and it is fully contemplated that all of the methods disclosed herein can be carried out by analog processing means and/or hybrid techniques using both digital and analog circuitry. Furthermore, several shorthand terms have been used throughout this disclosure, including "the $2^{nd}$ derivative of an image." One skilled in the art will readily recognize that an image cannot be subject to a derivative operation but the data that gives rise to the image can be manipulated mathematically (such as generating its derivative). It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed as new and desired to be protected by Letters Patent of the United States is:

1. A method of processing thermal graphic data, comprising the steps of:
   thermally disturbing a first specimen of known acceptable quality,
   collecting a first collection of thermal data from said first specimen as the temperature of the first specimen temporally deviates,
   converting said first collection of data into a first measure of variance,
   thermally disturbing a second specimen of unknown quality,
   collecting a second collection of thermal data from said second specimen as the temperature of the second specimen deviates,
   converting said second collection of data into a second measure of variance,
   comparing said first and second measures of variance to one another to determine if the second measure of variance is within a predetermined range of acceptability.

2. The method of claim 1, wherein at least one of the first and second measure of variance includes the step of:
   calculating the standard deviation of at least a portion of one of the first or second collection of thermal data.

3. The method of claim 1, wherein at least one of the first or second measures of variance include the step of:
   fitting a curve to at least one of the first or second collection of data.

4. The method of processing of thermographic data of claim 1, wherein said converting step further includes the substep of:
   creating a natural log (ln) transformation of said first collection of collected thermal data.

5. The method of processing of thermographic data of claim 1, wherein thermally disturbing the first specimen includes thermally disturbing the sample by applying an instantaneous heating or cooling pulse, a step heating or cooling pulse, a continuous heating or cooling pulse, or a modulated heating or cooling pulse.

6. The method of processing of thermographic data of claim 1, wherein converting said first collection of data step further includes:
   operating on said first collection of collected data using at least one of a least-squares linear piecewise function, a low-order polynomial, or a truncated Fourier series.

7. The method of processing of thermographic data of claim 1, wherein the comparing step further includes the step of:
   detecting the presence of one or more non-discrete defects of said specimen by comparing the first and second measures of variance.

8. The method of claim 1, further including thermally disturbing two or more specimens of known acceptable quality.

9. The method of claim 8, further including collecting a collection of data from each of said two or more specimens of known acceptable quality.

10. The method of claim 9, further including determining an expected range of variance from the data collected from each of said two or more specimens.

11. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said operating step further includes the step of:
      identifying discrete defects in a sample including identifying one or more pixels with a positive 2nd derivative peak followed by a negative 2nd derivative peak.

12. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said operating step further includes of the step of:
      identifying discrete defects in a sample that fall within a defined depth range including finding one or more pixels with a positive 2nd derivative peak followed by a negative 2nd derivative peak wherein the positive 2nd derivative peaks fall within a defined time range.

13. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said operating step further includes the step of:
      confirming that the sample is substantially similar to a predetermined standard including finding one or more pixels with a 2nd derivative peak time, peak time amplitude, and a zero crossing time behavior that substantially matches the behavior of the predetermined sample.

14. The method of binary processing of thermographic data, comprising the steps of:
   thermally disturbing a sample,
   collecting thermal data from said sample,
   converting said collected thermal data using a 2nd derivative function, and operating on said converted data using at least one binary classification operation,
   wherein said operating step further includes the step of:
      identifying portions of a sample that do not match corresponding portions of the predetermined standard including finding one or more pixels of the sample that do not have a 2nd derivative peak time, peak amplitude, width, and zero crossing time behavior that matches the behavior of the predetermined standard.

15. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said operating step further includes the step of:
      detecting anomalous boundary conditions on a back wall of the sample including identifying one or more pixels where a post-peak 2nd derivative includes an asymptotically negative portion.

16. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation
   wherein said operating step further includes the step of:
   detecting an inclusion for thermally conductive substrate coupled to said sample including detecting one or more pixels with only a negative peak.

17. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said converting data step further includes the step of:
      associating a peak of said 2nd derivative function with a constant width value.

18. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said converting data step further includes the steps of:
      associating a peak of said 2nd derivative function with a constant peak height value.

19. The method of binary processing of thermographic data, comprising the steps of:
   thermally disturbing a sample,
   collecting thermal data from said sample,
   converting said collected thermal data using a 2nd derivative function, and
   operating on said converted data using at least one binary classification operation,
   wherein said converting data step further includes correlating the timing of a peak of said 2nd derivative to a physical attribute of a subsurface attribute of said sample.

* * * * *

UNITED STATES PATENT AND TRADEMARK OFFICE
CERTIFICATE OF CORRECTION

PATENT NO.         : 8,449,176 B2
APPLICATION NO.    : 12/763992
DATED              : May 28, 2013
INVENTOR(S)        : Steven M. Shepard Page 1 of 1

It is certified that error appears in the above-identified patent and that said Letters Patent is hereby corrected as shown below:

On the Title page, section (74) Attorney, Agent or Firm – Honigman Miller Schwarz and Cohn LLP should be corrected to Honigman Miller Schwartz and Cohn LLP Signed and Sealed this
Twentieth Day of August, 2013

Teresa Stanek Rea
*Acting Director of the United States Patent and Trademark Office*